United States Patent
Tarunaga et al.

(10) Patent No.: US 10,850,075 B2
(45) Date of Patent: Dec. 1, 2020

(54) BALLOON CATHETER AND MANUFACTURING METHOD OF ELONGATED MEMBER FOR BALLOON CATHETER

(71) Applicant: TERUMO KABUSHIKI KAISHA, Tokyo (JP)

(72) Inventors: Akihiko Tarunaga, Shizuoka (JP); Kenta Suzuki, Shizuoka (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 180 days.

(21) Appl. No.: 16/131,710

(22) Filed: Sep. 14, 2018

(65) Prior Publication Data

US 2019/0009067 A1     Jan. 10, 2019

Related U.S. Application Data

(63) Continuation of application No. PCT/JP2017/010237, filed on Mar. 14, 2017.

(30) Foreign Application Priority Data

Mar. 16, 2016   (JP) ................................. 2016-053076

(51) Int. Cl.
*A61M 25/10*     (2013.01)
*B29D 23/00*     (2006.01)
(Continued)

(52) U.S. Cl.
CPC .......... *A61M 25/10* (2013.01); *A61M 25/104* (2013.01); *A61M 25/1025* (2013.01);
(Continued)

(58) Field of Classification Search
CPC .............. A61M 25/10; A61M 25/1025; A61M 25/104; A61M 2025/018; A61M 2025/0183; A61M 2025/1043
See application file for complete search history.

(56) References Cited

U.S. PATENT DOCUMENTS

| 5,156,594 A | 10/1992 | Keith |
| 2005/0059959 A1 | 3/2005 | Eidenschink |
| 2007/0142821 A1 | 6/2007 | Hennessy et al. |

FOREIGN PATENT DOCUMENTS

| JP | 06506124 A | 7/1994 |
| JP | 2005211308 A | 8/2005 |

(Continued)

OTHER PUBLICATIONS

English translation of the Written Opinion of the International Searching Authority dated Jul. 11, 2017 in International Application No. PCT/JP2017/010237.
(Continued)

*Primary Examiner* — Melanie R Tyson
(74) *Attorney, Agent, or Firm* — Buchanan Ingersoll & Rooney PC

(57) ABSTRACT

A balloon catheter is disclosed having a distal side shaft formed of a resin material, a proximal shaft formed of a metal material, and an inner tubular shaft disposed along an inclined portion and a concave portion of the proximal shaft. The distal side shaft is joined to the proximal shaft at the small diameter portion on the proximal side from a distal opening of the proximal shaft. The distal opening of the proximal shaft is disposed on the distal side from a guide wire proximal opening.

16 Claims, 8 Drawing Sheets

(51) Int. Cl.
    *B29C 63/00*     (2006.01)
    *B29C 63/42*     (2006.01)
    *B29C 69/00*     (2006.01)
    *A61M 25/01*     (2006.01)
    *B29L 31/00*     (2006.01)

(52) U.S. Cl.
    CPC ..... *A61M 25/1036* (2013.01); *B29C 63/0069* (2013.01); *B29C 63/42* (2013.01); *B29C 69/001* (2013.01); *B29D 23/00* (2013.01); *A61M 2025/018* (2013.01); *A61M 2025/0183* (2013.01); *A61M 2025/1043* (2013.01); *B29L 2031/7543* (2013.01)

(56) References Cited

FOREIGN PATENT DOCUMENTS

| | | | |
|---|---|---|---|
| JP | 2007505683 | A | 3/2007 |
| JP | 2008259695 | A | 10/2008 |
| JP | 2009519777 | A | 5/2009 |
| JP | 2014195487 | A | 10/2014 |

OTHER PUBLICATIONS

International Search Report (PCT/ISA/210) dated Jul. 11, 2017, by the Japanese Patent Office as the International Searching Authority for International Application No. PCT/JP2017/010237.

Written Opinion (PCT/ISA/237) dated Jul. 11, 2017, by the Japanese Patent Office as the International Searching Authority for International Application No. PCT/JP2017/010237.

BALLOON CATHETER AND MANUFACTURING METHOD OF ELONGATED MEMBER FOR BALLOON CATHETER

CROSS-REFERENCES TO RELATED APPLICATIONS

This application is a continuation of International Application No. PCT/JP2017/010237 filed on Mar. 14, 2017, which claims priority to Japanese Application No. 2016-053076 filed on Mar. 16, 2016, the entire contents of both of which is incorporated herein by reference.

TECHNICAL FIELD

The present disclosure generally relates to a balloon catheter, and a manufacturing method of an elongated member for a balloon catheter.

BACKGROUND ART

A balloon catheter is known as a medical device used in performing a medical procedure for widening a lesion area (stenosed site) formed in a living body lumen such as a blood vessel, or used in causing a stent to indwell the lesion area. As to types of balloon catheters, an over-the-wire type and a rapid exchange type are known.

The balloon catheter of the rapid exchange type is configured so that a guide wire is inserted into only a distal portion side of an elongated member called a catheter shaft having a balloon located in the catheter shaft. Therefore, a guide wire port (opening) through which the guide wire is inserted into or removed from the catheter shaft is disposed close to a distal portion in an axial direction of the catheter shaft.

As a manufacturing method of the catheter shaft used for the balloon catheter of the rapid exchange type, for example, a method disclosed in JP-A-2014-195487 has been proposed. According to this manufacturing method, the catheter shaft, which includes a distal side shaft, an inner tubular shaft, and a proximal shaft are fused to and integrated with each other. Note that, the inner tubular shaft is an inner tube having a guide wire lumen, and the distal side shaft and the proximal shaft comprise an outer tube having an inflation lumen through which a pressurizing medium for inflating the balloon can be circulated.

For example, in a manufacturing stage of the catheter shaft, if a tube wall is extremely thin, the guide wire lumen and the inflation lumen, which are disposed parallel to each other across the tube wall, may communicate with each other, thereby causing a possibility that leakage may occur between both the lumens. For this reason, according to the manufacturing method of the balloon catheter disclosed in JP-A-2014-195487, when a process of fusing and integrating the respective shafts to each other is performed, a predetermined connection tube is connected to a proximal portion side of the inner tubular shaft, thereby helping prevent a material for forming the inner tubular shaft from flowing into a proximal side and suppressing (or reducing) a possibility that the tube wall of the fused portion may be thinned (i.e., that the guide wire lumen and the inflation lumen are in communication with one another).

According to the manufacturing method using the above-described connection tube, if the tube is not fused in a state where the connection tube is accurately aligned with the proximal portion of the inner tubular shaft, an advantageous effect can be reduced in suppressing (or reducing) the possibility that the tube wall may be thinned. Therefore, since there is a possibility that the tube wall may be extremely thin due to slight misalignment of the connection tube, the above-described manufacturing method is not sufficient at all as a countermeasure to prevent the leakage from occurring.

In addition, according to the process of fusing three shafts such as the distal side shaft, the inner tubular shaft, and the proximal shaft, the respective shafts are disposed in a state where portions of the respective shafts overlap each other along an axial direction. Thereafter, heat and pressure are applied to the respective shafts from an outer peripheral side of the respective shafts. However, in the catheter shaft, a portion where the three shafts overlap each other along the axial direction, that is, a portion where the three shafts are fused to each other, has an increased outer peripheral length (outer diameter), compared to other portions. In a case of using the fusion method, it can be inevitable to form the portion where the outer peripheral length increases. Consequently, it can be difficult to form the catheter shaft so as to have the decreased outer peripheral length.

Furthermore, in a case of the catheter shaft formed by fusing the three shafts such as the distal side shaft, the inner tubular shaft and the proximal shaft, when a pushing force is transmitted from an operator's hand-side to a distal side, a transmission loss of the pushing force occurs at a joint of the respective shafts. Therefore, it can be difficult to provide the catheter shaft with sufficient pushing ability.

SUMMARY OF THE INVENTION

A balloon catheter is disclosed which can more reliably prevent leakage from a tube wall of an elongated member of a catheter shaft, which has a decreased outer peripheral length of the elongated member of the catheter shaft, and which has improved pushing ability. A manufacturing method is also disclosed for an elongated member for a balloon catheter which can be rather easily manufactured.

A balloon catheter is disclosed, which includes a distal side shaft formed of a resin material, a proximal shaft disposed on a proximal side of the distal side shaft and formed of a metal material, an inner tubular shaft disposed in a lumen of the distal side shaft and forming a guide wire lumen into which a guide wire is insertable, and a balloon fixed to a distal side of the inner tubular shaft and a distal side of the distal side shaft. The proximal shaft has a main body portion, an inclined portion disposed on a distal side of the main body portion and in which an outer peripheral surface of the proximal shaft is partially inclined, and a small diameter portion disposed on a distal side of the inclined portion and having a distal opening. In a cross section perpendicular to an axial direction of the proximal shaft, the small diameter portion has a concave portion recessed to a lumen side of the proximal shaft. The inner tubular shaft is disposed along the inclined portion and the concave portion, and is open on an outer surface of the distal side shaft so as to form a guide wire proximal opening. The distal side shaft is joined to the proximal shaft at the small diameter portion on the proximal side from the distal opening of the proximal shaft. The distal opening of the proximal shaft is disposed on the distal side from the guide wire proximal opening.

In addition, according to the present disclosure, a manufacturing method of an elongated member for a balloon catheter is disclosed. The method includes an assembly process including a preparation process of preparing a distal side shaft formed of a resin material, an inner tubular shaft formed of a resin material, and a proximal shaft formed of a metal material, the proximal shaft possessing a main body portion, an inclined portion which is disposed on a distal side of the main body portion and in which a portion of an outer peripheral surface is inclined, and a small diameter portion disposed on a distal side of the inclined portion and having a distal opening; an inner tubular shaft disposition process of disposing the inner tubular shaft in the lumen of the distal side shaft, a mandrel disposition process of inserting a mandrel into a lumen of the inner tubular shaft, and a proximal shaft disposition process of disposing the proximal shaft in the lumen of the distal side shaft while locating the inner tubular shaft along the inclined portion and the small diameter portion of the proximal shaft, a heat-shrinkable tube coating process of disposing a heat-shrinkable tube so as to cover a portion of the distal side shaft, and a joining process of joining the distal side shaft, the inner tubular shaft, and the proximal shaft to each other by heating and shrinking the heat-shrinkable tube.

According to the balloon catheter of the present disclosure, the inner tubular shaft is disposed along the inclined portion and the concave portion of the small diameter portion of the proximal shaft formed of the metal material. Accordingly, the lumen (guide wire lumen) of the inner tubular shaft can be prevented from communicating with the lumen (inflation lumen) of the proximal shaft in the vicinity of the guide wire proximal opening of the inner tubular shaft. Therefore, when an inflation fluid is injected into a balloon, it is possible to more reliably prevent leakage between the lumen of the inner tubular shaft and the lumen of the proximal shaft.

In addition, according to the balloon catheter of the present disclosure, in a portion where the elongated member (catheter shaft) includes three shafts such as the distal side shaft, the inner tubular shaft, and the proximal shaft, which are joined to each other, the inner tubular shaft is disposed in the concave portion of the proximal shaft. Accordingly, the outer peripheral length of the joined portion can be decreased. Therefore, it is possible to provide the elongated member having the decreased outer peripheral length.

In addition, according to the balloon catheter of the present disclosure, the proximal shaft formed of the metal material is joined to the distal side shaft and to the inner tubular shaft, and integrally extends to the distal side from the guide wire proximal opening. Accordingly, pushing ability of the elongated member (catheter shaft) is improved.

According to the manufacturing method of the elongated member for the balloon catheter of the present disclosure, while the inner tubular shaft is located along the inclined portion and the small diameter portion of the proximal shaft formed of the metal material, the proximal shaft disposition process of disposing the proximal shaft in the lumen of the distal side shaft is performed. In this manner, the lumen of the distal side shaft and the lumen of the proximal shaft are brought into a communication state. In the communication state, the joining process of joining the distal side shaft, the inner tubular shaft, and the proximal shaft to each other is performed. The proximal shaft is formed of the metal material. Accordingly, a cross-sectional shape of the proximal shaft can be prevented from being excessively deformed due to influence of heat and pressure which are applied when the joining process is performed. Accordingly, when the joining process is performed, it is not necessary to dispose the mandrel in order to form the inflation lumen between the lumen of the proximal shaft and the outer peripheral surface of the inner tubular shaft. Therefore, the elongated member for the balloon catheter can be rather easily manufactured.

A method is disclosed of manufacturing an elongated member for a balloon catheter, the method comprising: preparing a distal side shaft formed of a resin material, an inner tubular shaft formed of a resin material, and a proximal shaft formed of a metal material, the proximal shaft possessing a main body portion, an inclined portion which is disposed on a distal side of the main body portion and in which a portion of an outer peripheral surface is inclined, and a small diameter portion disposed on a distal side of the inclined portion and having a distal opening; disposing the inner tubular shaft in the lumen of the distal side shaft; inserting a mandrel into a lumen of the inner tubular shaft; disposing the proximal shaft in the lumen of the distal side shaft while locating the inner tubular shaft along the inclined portion and the small diameter portion of the proximal shaft; disposing a heat-shrinkable tube to cover a portion of the distal side shaft; and joining the distal side shaft, the inner tubular shaft, and the proximal shaft to each other by heating and shrinking the heat-shrinkable tube.

A treatment method is disclosed comprising: introducing a balloon catheter into a living body, the balloon catheter including a distal side shaft formed of a resin material, a proximal shaft disposed on a proximal side of the distal side shaft and formed of a metal material, the proximal shaft having a main body portion, an inclined portion disposed on a distal side of the main body portion and in which an outer peripheral surface of the proximal shaft is partially inclined, and a small diameter portion disposed on a distal side of the inclined portion and having a distal opening, and wherein in a cross section perpendicular to an axial direction of the proximal shaft, the small diameter portion having a concave portion recessed to a lumen side of the proximal shaft; and an inner tubular shaft disposed in a lumen of the distal side shaft and forming a guide wire lumen into which a guide wire is insertable, the inner tubular shaft being disposed along the inclined portion and the concave portion, the inner tubular shaft being open on an outer surface of the distal side shaft forming a guide wire proximal opening, and wherein the distal side shaft is joined to the proximal shaft at the small diameter portion on the proximal side from the distal opening of the proximal shaft, and the distal opening of the proximal shaft is disposed on the distal side from the guide wire proximal opening, and a balloon fixed to a distal side of the inner tubular shaft and a distal side of the distal side shaft; introducing a guide wire into the guide wire proximal opening; advancing the balloon catheter over the guide wire to a stenosed site in the living body; and inflating the balloon of the balloon catheter into the stenosed site.

DESCRIPTION OF EMBODIMENTS

Figure 1:
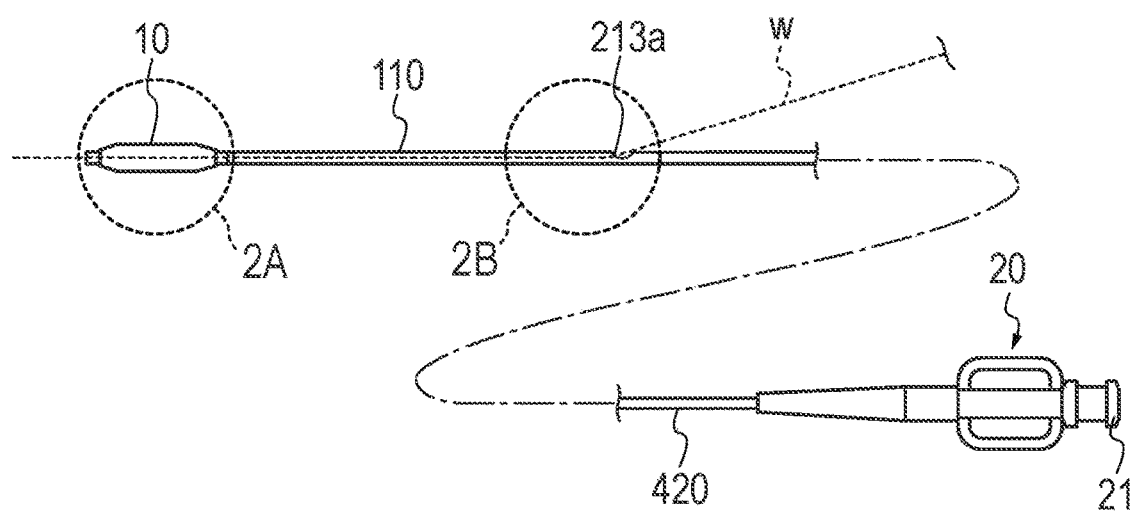
FIG. 1 is a view illustrating an overall configuration of a balloon catheter according to an embodiment.

Set forth below with reference to the accompanying drawings is a detailed description of embodiments of a balloon catheter and manufacturing method of an elongated member for a balloon catheter representing examples of the inventive balloon catheter disclosed here. In some cases, a dimension ratio in the drawings may be exaggerated and different from a ratio used in practice in order to facilitate the description.

Hereinafter, referring to FIGS. 1 to 10B, a balloon catheter 1 according to the present embodiment and a manufacturing method of a catheter shaft 110 (corresponding to an elongated member for a balloon catheter) used as a configuration member of the balloon catheter 1 will be described.

Figure 2A:
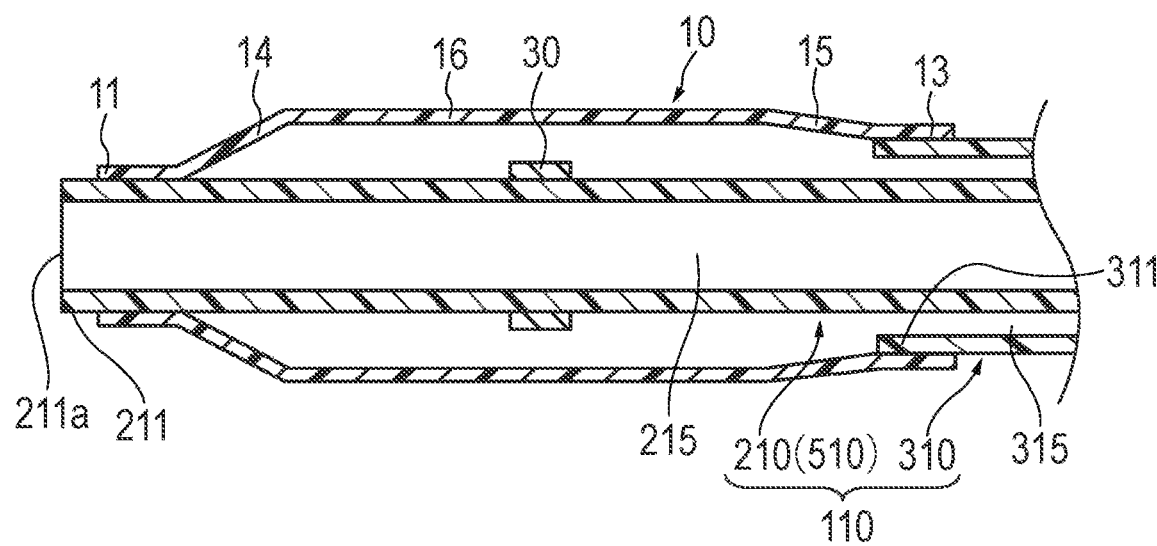
FIG. 2A is a cross-sectional view taken along an axial direction of a portion surrounded by a broken line portion 2A in FIG. 1.
Figure 2B:
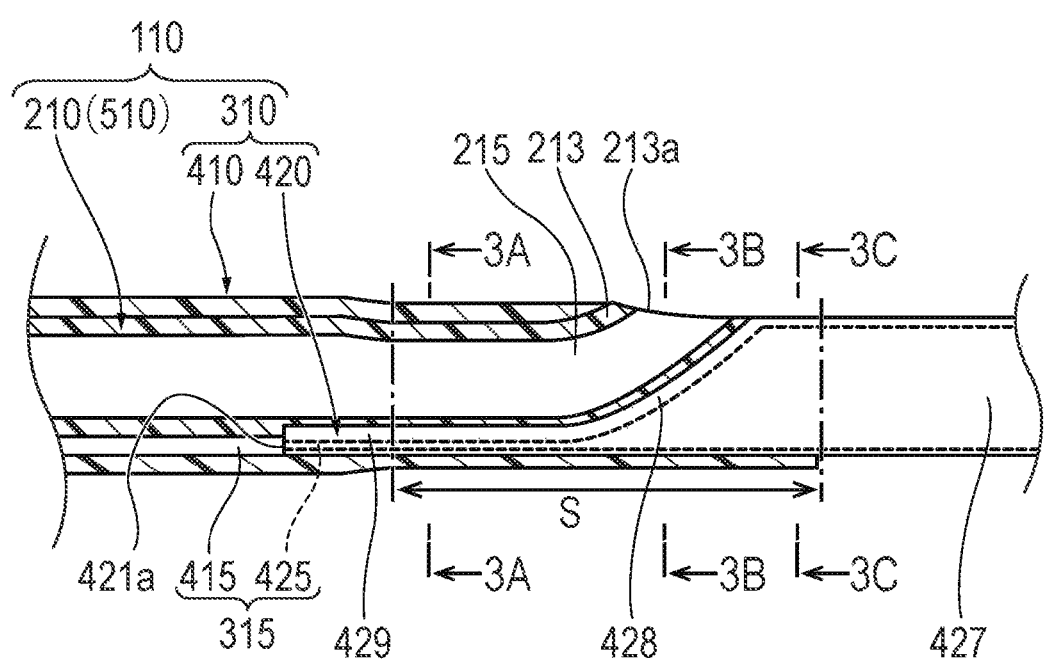
FIG. 2B is a cross-sectional view taken along the axial direction of a portion surrounded by a broken line portion 2B in FIG. 1.
Figure 3A:
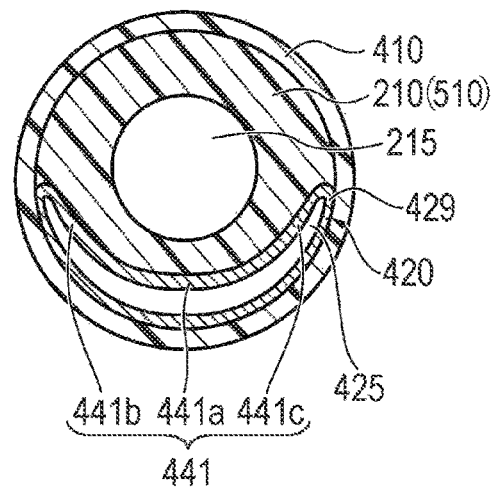
FIG. 3A is a cross-sectional view taken along arrow 3A-3A illustrated in FIG. 2B.
Figure 3B:
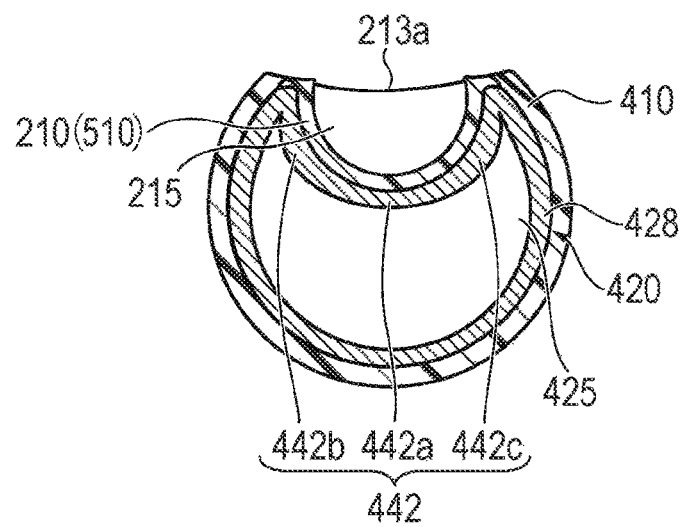
FIG. 3B is a cross-sectional view taken along arrow 3B-3B illustrated in FIG. 2B.
Figure 3C:
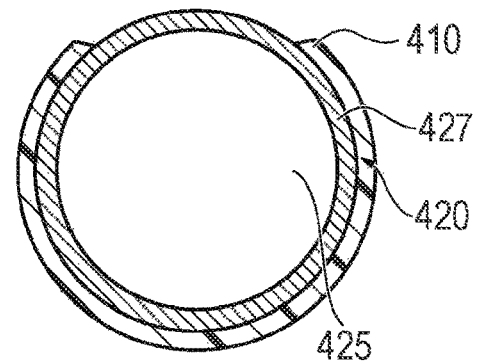
FIG. 3C is a cross-sectional view taken along arrow 3C-3C illustrated in FIG. 2B.
Figure 4A:
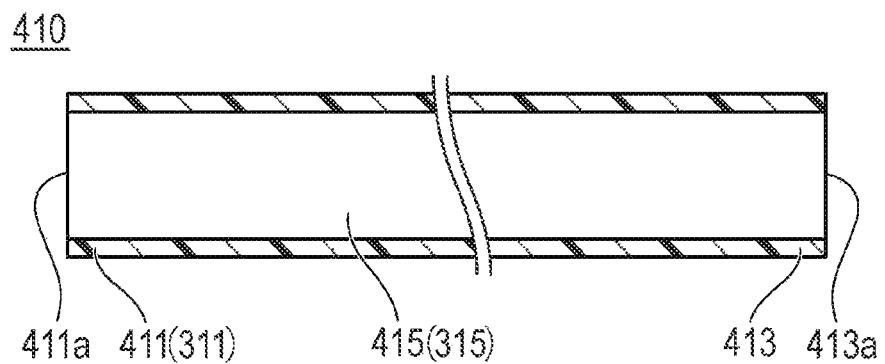
FIG. 4A is a cross-sectional view of a distal side shaft along the axial direction.
Figure 4B:
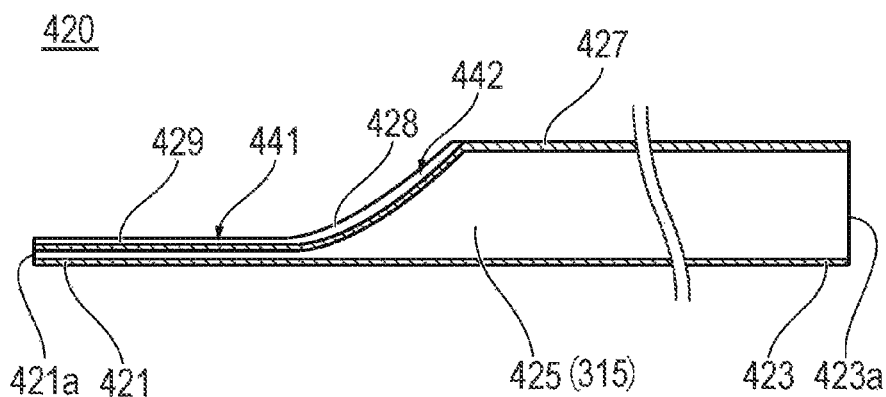
FIG. 4B is a cross-sectional view of a proximal shaft along the axial direction.
Figure 4C:
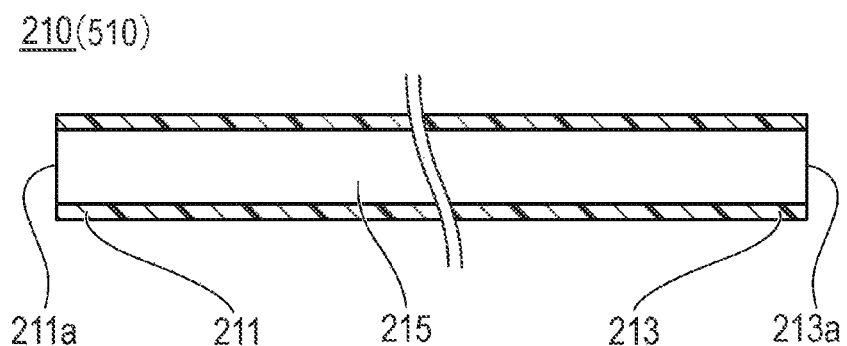
FIG. 4C is a cross-sectional view of an inner tubular shaft along the axial direction.
Figure 5A:
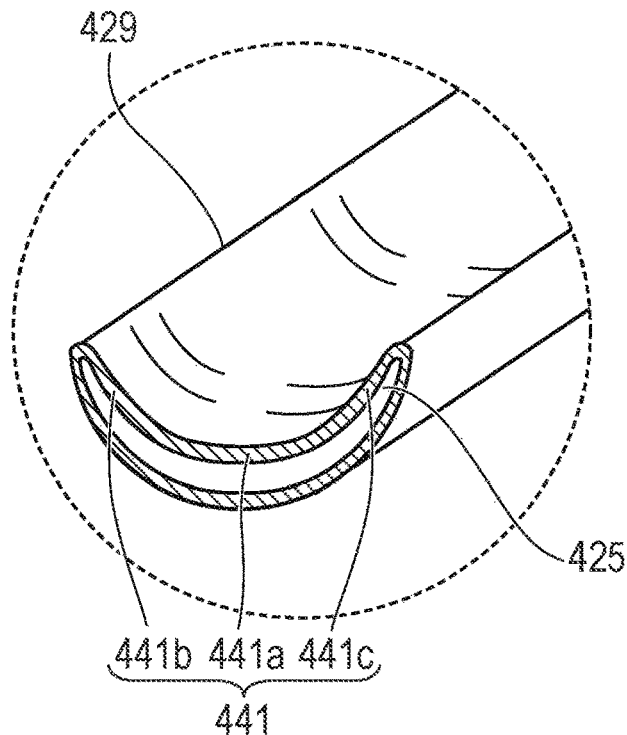
FIG. 5A is a perspective cross-sectional view of a small diameter portion of the proximal shaft.
Figure 5B:
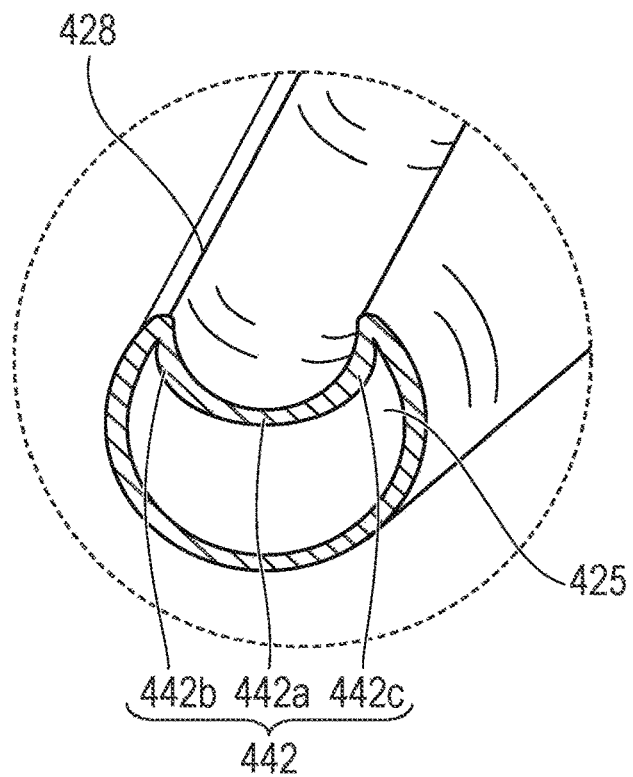
FIG. 5B is a perspective cross-sectional view of an inclined portion of the proximal shaft.

FIGS. 1 to 3C illustrate a configuration of each portion of the balloon catheter 1, and FIGS. 4A to 4C illustrate the catheter shaft 110, which includes a distal side shaft 410, a proximal shaft 420, and an inner tubular shaft 510. FIG. 5A illustrates a small diameter portion 429 of the proximal shaft 420, and FIG. 5B illustrates an inclined portion 428 of the proximal shaft 420. FIGS. 6 to 10B illustrate views for describing each process of the manufacturing method of the catheter shaft 110.

In the description herein, a side (side for disposing a balloon 10) to be inserted into a living body lumen in the balloon catheter 1 and the catheter shaft 110 is referred to as a distal side, and a side (side for disposing a hub 20) located opposite to the distal side and operated by an operator's hand is referred to as a proximal side. In addition, a direction in which the catheter shaft 110 stretches is referred to as an axial direction.

First, referring to FIGS. 1 to 3C, a configuration of each portion of the balloon catheter 1 will be described.

As illustrated in FIG. 1, the balloon catheter 1 has a flexible and elongated catheter shaft 110, a balloon 10 disposed on the distal portion side of the catheter shaft 110, and a hub 20 disposed on the proximal portion side of the catheter shaft 110.

The balloon catheter 1 is a medical device for performing treatment as follows. The catheter shaft 110 is inserted into a living body lumen such as a blood vessel, and the balloon 10 disposed on the distal portion side is inflated in a lesion area (stenosed site), thereby widening the lesion area. A guide wire proximal opening 213a into which a guide wire w is introduced is disposed close to the distal portion side of the catheter shaft 110. The balloon catheter 1 according to the present embodiment is configured to serve as a so-called rapid exchange type catheter.

As illustrated in FIG. 2A, the catheter shaft 110 has an outer tube 310 including a predetermined lumen 315, and an inner tube 210 disposed in a lumen 315 of the outer tube 310 and including a guide wire lumen 215 into which the guide wire w is insertable.

As will be described later, the outer tube 310 has a distal side shaft 410 and a proximal shaft 420 (refer to FIGS. 4A and 4B). In addition, the inner tube 210 has an inner tubular shaft 510 (refer to FIG. 4C).

A distal tip which can help prevent an inner wall of the living body lumen from being damaged can be attached to the distal side of the inner tube 210. For example, the distal tip can include a tubular member which is more flexible than the inner tube 210.

The outer tube 310 extends from the vicinity of a proximal portion 13 of the balloon 10 to the hub 20 (refer to FIGS. 1 and 2A). As illustrated in FIG. 1, the proximal side of the outer tube 310 has a proximal shaft 420 made of metal. The proximal shaft 420 extends to the hub 20 without being connected to other resin or metal shafts on the proximal side. For example, the proximal side of the proximal shaft 420 can be provided with a depth marker indicating a scale of an insertion depth of the balloon catheter inserted into the living body or the guiding catheter.

The lumen 315 included in the outer tube 310 communicates with an interior of the balloon 10 on the distal side. The lumen 315 is used as an inflation lumen for circulating an inflation fluid to inflate the balloon 10.

As illustrated in FIGS. 2A and 2B, the inner tube 210 includes two openings such as a distal opening 211a formed in a distal portion 211 and the guide wire proximal opening 213a formed in a proximal portion 213.

The guide wire lumen 215 communicates with the respective openings 211a and 213a. The guide wire proximal opening 213a has a guide wire port used as an inlet when the guide wire w is inserted into the guide wire lumen 215 and an outlet when the guide wire w is pulled out from the guide wire lumen 215.

As illustrated in FIG. 2A, the balloon 10 has an effectively inflatable portion (pressurizing portion) 16 having a relatively straight shape which is inflated and deformed so as to widen the stenosed site formed inside the living body lumen, a distal side tapered portion 14 located on the distal side of the effectively inflatable portion 16, and a proximal side tapered portion 15 located on the proximal side of the effectively inflatable portion 16.

The balloon 10 is fixed (i.e., attached) to the distal side of the inner tube 210 and to the distal side of the outer tube 310. More specifically, the distal portion 11 of the balloon 10 is fixed to an outer surface of the distal portion 211 of the inner tube 210, and the proximal portion 13 of the balloon 10 is fixed to an outer surface of a distal portion 311 of the outer tube 310.

The balloon 10 material is not particularly limited. For example, the balloon 10 material can be polyolefin such as polyethylene, polypropylene, and ethylene-propylene copolymer, polyester such as polyethylene terephthalate, polyvinyl chloride, ethylene-vinyl acetate copolymer, cross-linked ethylene-vinyl acetate copolymer, thermoplastic resin such as polyurethane, polyamide, polyamide elastomer, polystyrene elastomer, silicone rubber, or latex rubber.

As illustrated in FIG. 1, the hub 20 includes a connection section 21 which can be air-tightly and liquid-tightly connected to a supply device (not illustrated) such as an indeflator for supplying the inflation fluid. For example, the connection section 21 of the hub 20 can be a known Luer taper configured so that a fluid tube can be connected to the connection section 21 of the hub 20 and separated from the connection section 21 of the hub 20. The inflation fluid (for example, a saline or a contrast agent) can be caused to flow into the lumen 315 of outer tube 310 included in the catheter shaft 110 via the connection section 21 of the hub 20.

As illustrated in FIG. 2A, the inner tube 210 is provided with an X-ray contrast marker 30 indicating a central position in the axial direction of the effectively inflatable portion 16 of the balloon 10. For example, the X-ray contrast marker 30 can be a metal such as platinum, gold, silver, iridium, titanium, and tungsten, or an alloy of the metals.

As illustrated in FIG. 2B, a predetermined joint region S is formed in the vicinity of the guide wire proximal opening 213a. In the joint region S, the inner tubular shaft 510, the distal side shaft 410, and the proximal shaft 420 are joined to each other. Specifically, the inner tubular shaft 510 and the distal side shaft 410 which are formed of a resin material are fused to each other, and the proximal shaft 420 and each of the shafts 410 and 510 which are formed of a metal material are fused to each other.

Next, referring to FIGS. 4A to 4C, the distal side shaft 410, the proximal shaft 420, and the inner tubular shaft 510 will be described.

As illustrated in FIG. 4A, the distal side shaft 410 is a tubular member having a constant inner diameter and outer diameter along the axial direction. An axially orthogonal cross section of the distal side shaft 410 is formed in a circular shape. However, without being particularly limited to the any particular shape, the shape may be a rectangle, a triangle, or an ellipse.

The distal side shaft 410 has a distal portion 411 having a distal opening 411a formed in the distal side shaft 410, a proximal portion 413 having a proximal opening 413a formed in the proximal portion 413, and a lumen 415 connected to the distal opening 411a and the proximal opening 413a.

The distal portion 411 of the distal side shaft 410 forms the distal portion 311 of the outer tube 310 (refer to FIG. 2A). The lumen 415 of the distal side shaft 410 forms the lumen (inflation lumen) 315 of the outer tube 310 together with the lumen 425 of the proximal shaft 420 (refer to FIG. 2B).

The distal side shaft 410 is formed of a resin material. For example, the distal side shaft 410 material can be polyolefin such as polyethylene, polypropylene, polybutene, ethylene-propylene copolymer, ethylene-vinyl acetate copolymer, ionomer, or a mixture of two or more materials of the polyolefins, or fluororesins, such as soft polyvinyl chloride resin, polyamide, polyamide elastomer, polyester, polyester elastomer, polyurethane, and polytetrafluoroethylene.

As illustrated in FIG. 4B, the proximal shaft 420 has a main body portion 427, an inclined portion 428 which is disposed on the distal side of the main body portion 427 and in which a portion of the outer peripheral surface of the proximal shaft 420 is inclined, and a small diameter portion 429 which is disposed on the distal side of the inclined portion 428 and which has a distal opening 421a.

The main body portion 427 is formed to have a substantially constant inner diameter along the axial direction and a substantially constant outer diameter along the axial direction. In a cross section taken along the axial direction of the proximal shaft 420 illustrated in FIG. 4B, the main body portion 427 is formed to have the largest width of the lumen and the largest width of the outer shape, compared to other portions of the proximal shaft 420. The inclined portion 428 is formed between the main body portion 427 and the small diameter portion 429. Then, in the cross section taken along the axial direction of the proximal shaft 420 illustrated in FIG. 4B, in the inclined portion 428, the width of the lumen and the width of the outer shape gradually decrease from the main body portion 427 side toward the small diameter portion 429 side. The small diameter portion 429 is formed to have a substantially constant inner diameter along the axial direction and a substantially constant outer diameter along the axial direction. Then, in the cross section taken along the axial direction of the proximal shaft 420 illustrated in FIG. 4B, the small diameter portion 429 is formed to have the smallest width of the lumen and the smallest width of the outer shape, compared to other portions of the proximal shaft 420.

The lumen 425 of the proximal shaft 420 communicates with the distal opening 421a and a proximal opening 423a. A cross-sectional area of the lumen 425 is formed to have a size varying in the axial direction in accordance with a change in the width of the lumen of the respective portions 427, 428, and 429. That is, the cross-sectional area of the lumen 425 is the largest in the main body portion 427, gradually decreases from the inclined portion 428 toward the small diameter portion 429, and is the smallest in the small diameter portion 429.

The proximal shaft 420 has no hole or opening to communicate with the outside except for the respective openings 421a and 421b. Therefore, the lumen 425 of the proximal shaft 420 communicates with the outside, only through the distal opening 421a and the proximal opening 423a. Specifically, the proximal shaft 420 has no hole formed so that a resin forming the distal side shaft 410 and the inner tubular shaft 510 enters the lumen of the proximal shaft 420 from the outer surface of the proximal shaft 420 in a joining process to be described later.

FIG. 3A illustrates an axially orthogonal cross section (cross section perpendicular to the axial direction of the proximal shaft 420) taken along an arrow 3A-3A illustrated in FIG. 2B. As illustrated in FIG. 3A, the small diameter portion 429 of the proximal shaft 420 has a concave portion 441 recessed to the lumen 425 side (i.e., of the proximal shaft 420 in the axially orthogonal cross section.

In the axially orthogonal cross section, the concave portion 441 has a first curved portion 441a curved (for example, mostly or to the greatest extent) to the lumen 425 side of the proximal shaft 420, and a second curved portion 441b and a third curved portion 441c which are curved outward (radially outward) of the guide wire lumen 215 while being apart from the first curved portion 441a. The second curved portion 441b and the third curved portion 441c are substantially symmetrical with each other in the cross section perpendicular to the axial direction of the proximal shaft 420.

The first curved portion 441a is disposed substantially at the center of the axially orthogonal cross section, and is provided with a shape whose curvature is small and which is slightly curved, compared to the other curved portions 441b and 441c. The second curved portion 441b extends along a circumferential direction from one end portion (left end portion in FIG. 3A) of the first curved portion 441a toward the outer surface of the inner tubular shaft 510, and is disposed so as to overlap the guide wire lumen 215 in the circumferential direction. Similarly, the third curved portion 441c extends along the circumferential direction from the other end portion (right end portion in FIG. 3A) of the first curved portion 441a toward the outer surface of the inner tubular shaft 510, and is disposed so as to overlap the guide wire lumen 215 in the circumferential direction.

FIG. 5A illustrates a perspective cross-sectional view of the concave portion 441 of the small diameter portion 429. The small diameter portion 429 has the concave portion 441. Accordingly, the small diameter portion 429 has a cross-sectional shape of a substantially crescent shape whose center portion of the small diameter portion 429 is curved downward (for example, mostly or to the greatest extent) in the circumferential direction and whose both end sides are curved upward in the circumferential direction. The cross-sectional shape is formed continuously along the axial direction.

FIG. 3B illustrates an axially orthogonal cross section (cross section perpendicular to the axial direction of the proximal shaft 420) taken along an arrow 3B-3B illustrated in FIG. 2B. As illustrated in FIG. 3B, in the axially orthogonal cross section, the inclined portion 428 of the proximal shaft 420 has a proximal side concave portion 442 recessed to the lumen 425 side of the proximal shaft 420.

In the axially orthogonal cross section, the proximal side concave portion 442 has a first curved portion 442a curved (for example, mostly or to the greatest extend) to the lumen 425 side of the proximal shaft 420, and a second curved portion 442b and a third curved portion 442c which are curved outward (radially outward) of the guide wire lumen 215 while being apart from the first curved portion 442a. The second curved portion 442b and the third curved portion 442c are substantially symmetrical with each other in the cross section perpendicular to the axial direction of the proximal shaft 420.

The first curved portion 442a is disposed at substantially the center of the axially orthogonal cross section, and has a curvature smaller than that of the other curved portions 442b and 442c. The second curved portion 442b extends along the circumferential direction from one end portion (left end portion in FIG. 3B) of the first curved portion 442a toward the outer surface of the inner tubular shaft 510, and is disposed so as to overlap the guide wire lumen 215 in the circumferential direction. Similarly, the third curved portion 442c extends along the circumferential direction from the other end portion (right end portion in FIG. 3B) of the first curved portion 442a toward the outer surface of the inner tubular shaft 510, and is disposed so as to overlap the guide wire lumen 215 in the circumferential direction.

If the concave portion 441 of the small diameter portion 429 and the proximal side concave portion 442 of the inclined portion 428 are compared with each other, the concave portion 441 is curved at an overall curvature which is smaller than that of the proximal side concave portion 442. That is, compared to the proximal side concave portion 442, the concave portion 441 has a shape which is curved in a relatively gentle and flat shape in a rightward-leftward direction in the axially orthogonal cross section.

FIG. 5B illustrates a perspective cross-sectional view of the proximal side concave portion 442 of the inclined portion 428. The proximal side concave portion 442 is formed along the outer surface of the inclined portion 428, and extends to a boundary between the inclined portion 428 and the main body portion 427. Note that, although not illustrated, the concave portion 441 of the small diameter portion 429 and the proximal side concave portion 442 of the inclined portion 428 are continuously formed without being cut off at the boundary between the small diameter portion 429 and the inclined portion 428.

The proximal shaft 420 is formed of a metal material. For example, as a material for forming the proximal shaft 420, it is possible to use aluminum, stainless steel, SUS (aka, stainless steel), brass, or Ni—Ti (nickel titanium or nitinol). Note that, a shaft having a reinforcement body for preventing kink occurrence by adjusting rigidity of the catheter shaft 110 may be appropriately connected to the proximal side of the proximal shaft 420.

As illustrated in FIG. 4C, the inner tubular shaft 510 is configured to include a tubular member provided with an inner diameter which is constant along the axial direction and an outer diameter which is constant along the axial direction. A shape of an axially orthogonal cross section of the inner tubular shaft 510 is circular. However, without being particularly limited to any particular shape, the shape may be a rectangle, a triangle, or an ellipse.

The inner tubular shaft 510 has a distal portion 211 having a distal opening 211a formed in the distal portion 211, a proximal portion 213 having a proximal opening 213a formed in the proximal portion 213, and a lumen 215 connected to the distal opening 211a and the proximal opening 213a.

The lumen 215 of the inner tubular shaft 510 is the guide wire lumen, and the proximal opening 213a of the inner tubular shaft 510 is the guide wire proximal opening (refer to FIG. 2A).

The inner tubular shaft 510 is formed of a resin material. For example, as a material for forming the inner tubular shaft 510, it is possible to use a material which is the same as the material for forming the distal side shaft 410.

A colorant can be included in the vicinity of the distal side for disposing the balloon 10 of the inner tubular shaft 510 and in the vicinity of the proximal side for forming the proximal opening (guide wire proximal opening) 213a. In this manner, these portions can be formed with relatively low transparency. On the other hand, an intermediate portion between the vicinity of the distal side of the inner tubular shaft 510 and the vicinity of the proximal side can be formed with a relatively higher transparency compared to other portions.

As described above, the vicinity of the proximal side of the inner tubular shaft 510 is formed with the relatively low transparency. In this manner, when the balloon catheter 1 is used, a position of the guide wire proximal opening 213a can be rather easily recognized. In addition, when the catheter shaft 110 is manufactured, the position of the guide wire proximal opening 213a can be rather easily recognized. Accordingly, manufacturing work efficiency can be improved. In addition, as described above, the intermediate portion of the inner tubular shaft 510 is formed with the relatively high transparency. In this manner, a joined state of the joint region S can be visibly confirmed, and product quality can be improved. Note that, in a case where the intermediate portion of the inner tubular shaft 510 is formed with the relatively high transparency, in order to enable the joined state of the joint region S to be confirmed, it is preferable that the distal side shaft 410 also has the relatively highly transparent portion.

Next, referring to FIGS. 2B and 3A to 3C, a disposition relationship of the respective shafts 410, 420, and 510 in the vicinity of the joint region S will be described.

As illustrated in FIG. 2B, in the joint region S, the inner tubular shaft 510 (inner tube 210) is disposed in the inclined portion 428 and the small diameter portion 429. More specifically, as illustrated in FIGS. 3A and 3B, the inner tubular shaft 510 is disposed along the concave portion 441 of the small diameter portion 429 and the proximal side concave portion 442 of the inclined portion 428.

In addition, as illustrated in FIG. 2B, the distal side shaft 410 is joined to the proximal shaft 420 at the small diameter portion 429 located on the proximal side from the distal opening 421a of the proximal shaft 420. In addition, the distal opening 421a of the proximal shaft 420 is disposed on the distal side from the guide wire proximal opening 213a.

As described above, the inner tubular shaft 510 is disposed along the inclined portion 428 of the proximal shaft 420 formed of the metal material and the concave portion 441 of and the small diameter portion 429. Accordingly, during a joining process to be described later, the guide wire lumen 215 can be prevented from communicating with the lumen 415 of the distal side shaft 410 in the vicinity of the guide wire proximal opening 213a. Furthermore, in the joint region S where the three shafts such as the distal side shaft 410, the inner tubular shaft 510, and the proximal shaft 420 are joined to each other, the inner tubular shaft 510 is disposed in the respective concave portions 441 and 442 of the proximal shaft 420. Accordingly, an outer peripheral length (outer diameter) of the joint region S can be decreased. In addition to these configurations, the proximal shaft 420 formed of the metal material is joined to the distal side shaft 410 and the inner tubular shaft 510, and integrally extends to the distal side from the guide wire proximal opening 213a. Accordingly, pushing ability of the catheter shaft 110 can be improved.

As illustrated in FIG. 3A, at least a portion of the guide wire lumen 215 is surrounded by the concave portion 441 of the small diameter portion 429 in the axially orthogonal cross section. The "surrounded by the concave portion 441" described herein means that the concave portion 441 overlaps a portion of the guide wire lumen 215 in a direction orthogonal to the axial direction of the proximal shaft 420. Note that, the concave portion 441 may not overlap the whole guide wire lumen 215 in the direction orthogonal to the axial direction of the proximal shaft 420. For example, as illustrated in FIG. 3A, the concave portion 441 may overlap the portion of the guide wire lumen 215 in the direction orthogonal to the axial direction of the proximal shaft 420.

In addition, as illustrated in FIG. 3B, in the vicinity of the guide wire proximal opening 213a, at least a portion of the guide wire lumen 215 is surrounded by the proximal side concave portion 442 of the inclined portion 428 in the axially orthogonal cross section. Note that, the proximal side concave portion 442 may not overlap the whole guide wire lumen 215 in the direction orthogonal to the axial direction of the proximal shaft 420. For example, as illustrated in FIG. 3B, the proximal side concave portion 442 may overlap the portion of the guide wire lumen 215 in the direction orthogonal to the axial direction of the proximal shaft 420.

As illustrated in FIG. 3C, in the joint region S of the proximal side from the guide wire proximal opening 213a, a portion of the outer peripheral surface of the main body portion 427 of the proximal shaft 420 and the distal side shaft 410 are fused to each other.

Next, referring to FIGS. 6 to 10B, a manufacturing method of the catheter shaft 110 will be described. Here, each process of joining the distal side shaft 410, the proximal shaft 420, and the inner tubular shaft 510 (inner tube 210) in the vicinity of the guide wire proximal opening 213a will be described in detail.

First, a preparation process is performed.

In the preparation process, the distal side shaft 410, the proximal shaft 420, and the inner tubular shaft 510, which form the catheter shaft 110, are prepared (refer to FIGS. 4A to 4C).

Next, an assembly process is performed. The assembly process includes an inner tubular shaft disposition process, a mandrel disposition process, and a proximal shaft disposition process.

Figure 6:
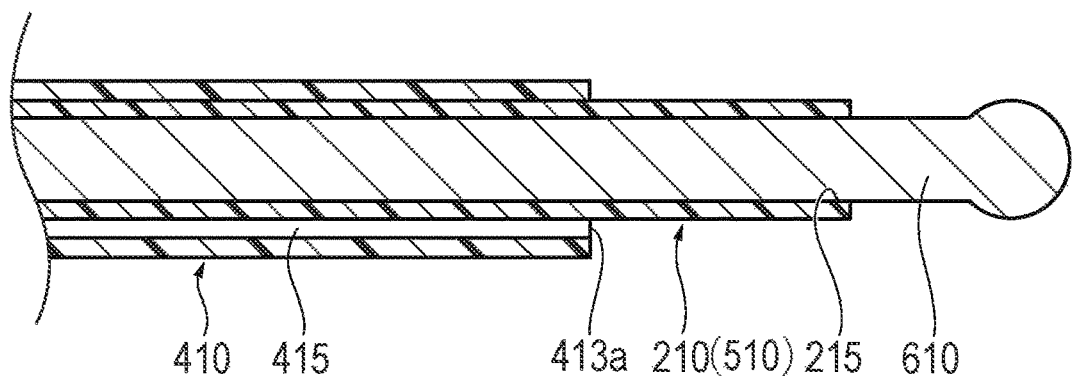
FIG. 6 is a view for describing a manufacturing method of an elongated member for a balloon catheter according to an embodiment, and is a view illustrating a state of an assembly process.

As illustrated in FIG. 6, the inner tubular shaft 510 is inserted into the distal side shaft 410, and the inner tubular shaft 510 is disposed in the lumen 415 of the distal side shaft 410 (inner tubular shaft disposition process).

Next, as illustrated in FIG. 6, a mandrel (core bar) 610 is inserted into the lumen 215 of the inner tubular shaft 510 (mandrel disposition process).

Figure 7:
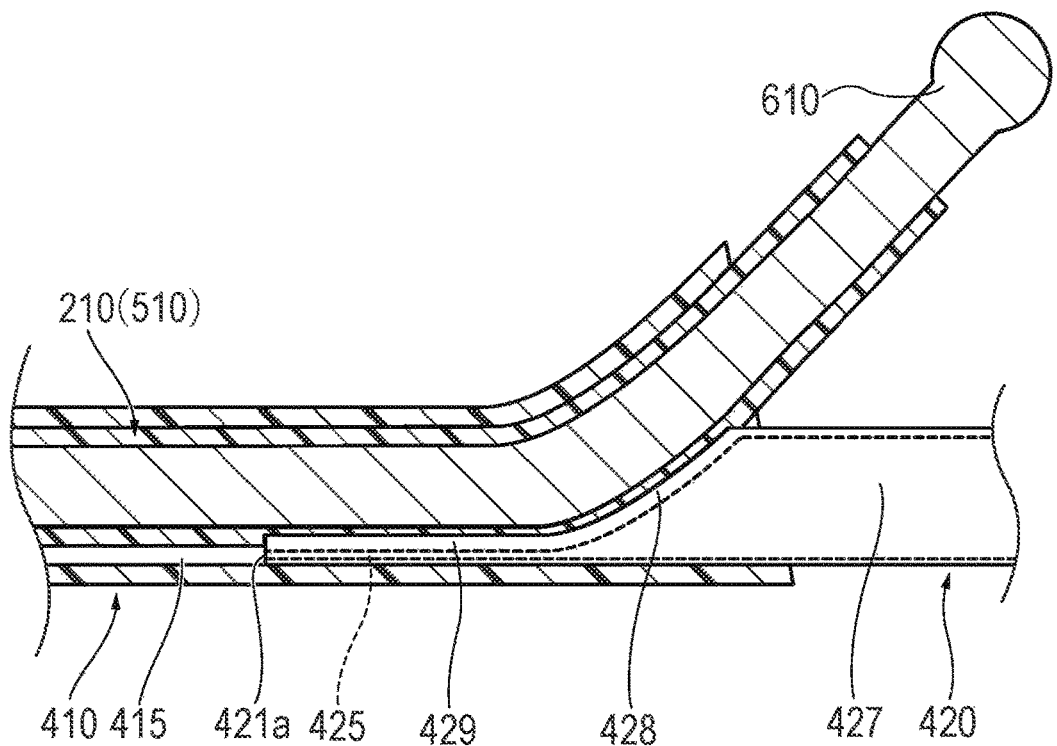
FIG. 7 is a view for describing a manufacturing method of the elongated member for the balloon catheter according to the embodiment, and is a view illustrating a state of the assembly process.

Next, as illustrated in FIG. 7, while the inner tubular shaft 510 is located along the inclined portion 428 and the small diameter portion 429 of the proximal shaft 420, the proximal shaft 420 is disposed in the lumen 415 of the distal side shaft 410 (proximal shaft disposition process). In this case, the proximal shaft 420 can be smoothly inserted by locating the inner tubular shaft 510 along the concave portion 441 of the small diameter portion 429 and the proximal side concave portion 442 of the inclined portion 428. In addition, the inner tubular shaft 510 is disposed in the concave portion 441 and the proximal side concave portion 442. In this manner, the inner tubular shaft 510 can be prevented from being displaced from the small diameter portion 429 or the inner tubular shaft 510 can be prevented from being displaced from the inclined portion 428.

When the proximal shaft 420 is inserted into the lumen 415, the proximal shaft 420 is pushed into the distal side shaft 410. In this manner, the proximal side of the distal side shaft 410 is expanded as illustrated in FIG. 7. In addition, the proximal shaft 420 is inserted into the distal side shaft 410, thereby bringing the lumen 415 and the lumen 425 into a communication state.

Next, a heat-shrinkable tube coating process is performed. The heat-shrinkable tube coating process includes a heat-shrinkable tube disposition process.

Figure 8:
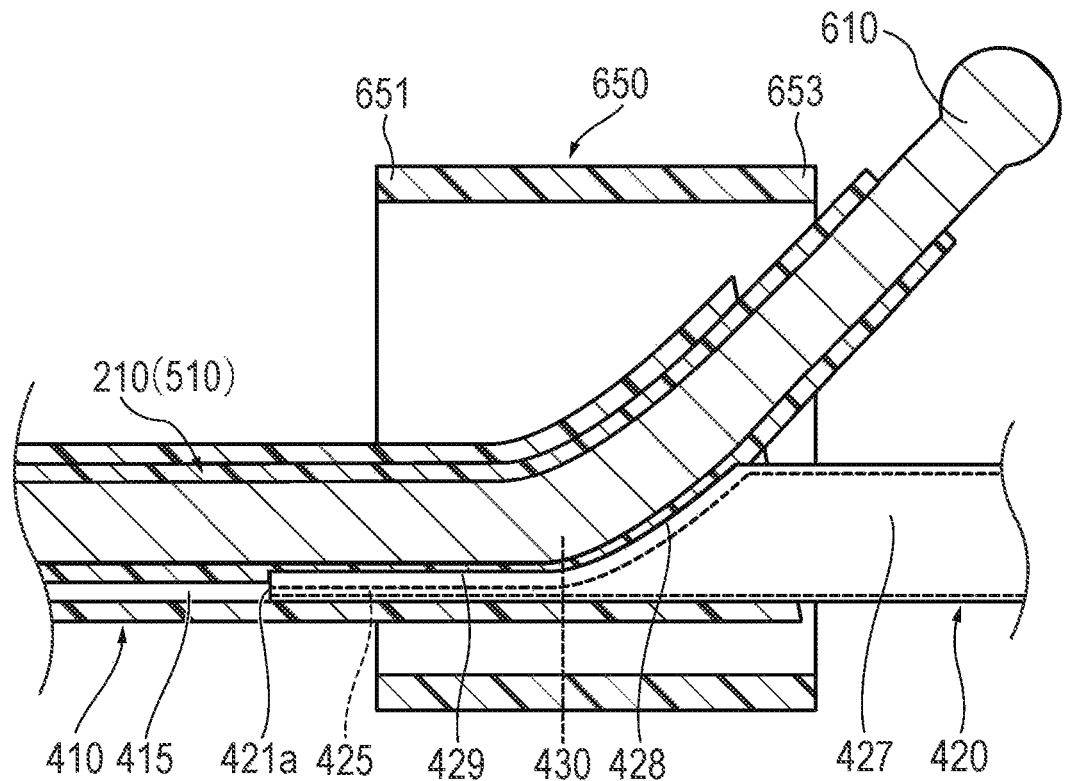
FIG. 8 is a view for describing a manufacturing method of the elongated member for the balloon catheter according to the embodiment, and is a view illustrating a state of a heat-shrinkable tube coating process.

As illustrated in FIG. 8, a heat-shrinkable tube 650 is disposed so as to cover the proximal side of the distal side shaft 410. In this case, the distal portion 651 of the heat-shrinkable tube 650 is disposed on the proximal side from the distal opening 421a of the proximal shaft 420, which is the distal side from a boundary portion 430 between the small diameter portion 429 and the inclined portion 428. A proximal portion 653 of the heat-shrinkable tube 650 is disposed on the proximal side from the proximal portion 653 of the distal side shaft 410 (heat-shrinkable tube disposition process).

For example, as the heat-shrinkable tube 650, a hollow cylindrical member configured to include polyolefin can be used. For example, the heat-shrinkable tube 650 may be disposed by being inserted from the distal side of the respective shafts 410, 420, and 510, or may be disposed by being inserted from the proximal side of the respective shafts 410, 420, and 510.

Next, a joining process is performed.

The heat-shrinkable tube 650 is heated and shrunk so as to join the distal side shaft 410, the proximal shaft 420, and the inner tubular shaft 510 to each other. When the heat-shrinkable tube 650 is heated, the heat-shrinkable tube 650 contracts, and is deformed so that the inner diameter after being heated is smaller than the inner diameter before being heated. Therefore, in a state where the heat-shrinkable tube 650 is attached to the outer periphery of the distal side shaft 410 and the proximal shaft 420, the heat-shrinkable tube 650 is heated. In this manner, pressure can be applied to the distal side shaft 410, the proximal shaft 420, and the inner tubular shaft 510 from the outside toward the inside.

The proximal shaft 420 is formed of the metal material. Accordingly, a cross-sectional shape of the proximal shaft 420 can be prevented from being excessively deformed due to influence of heat and pressure which are applied when the joining process is performed. Therefore, it is not necessary to dispose the mandrel in order to form the inflation lumen 315 between the lumen 425 of the proximal shaft 420 and the outer peripheral surface of the inner tubular shaft 510.

Figure 9:
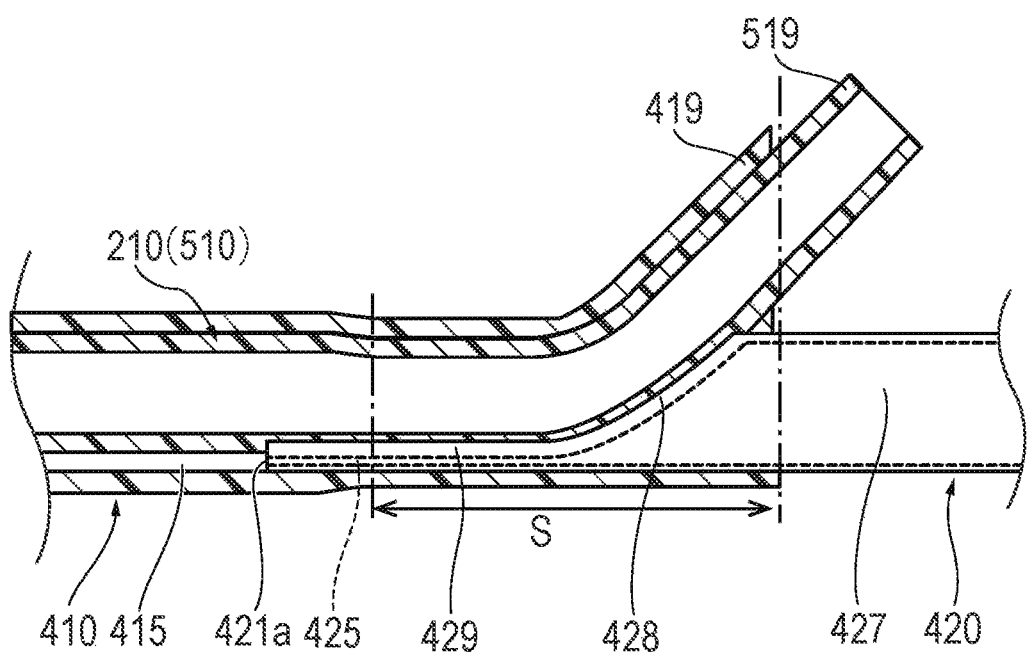
FIG. 9 is a view for describing a manufacturing method of the elongated member for the balloon catheter according to the embodiment, and is a view illustrating each shaft after a joining process is performed.

The joining process is performed, thereby forming the joint region S as illustrated in FIG. 9. In the joint region S, the proximal shaft 420 formed of the metal material and the distal side shaft 410 formed of the resin material are fused to each other. Similarly, the proximal shaft 420 formed of the metal material and the inner tubular shaft 510 formed of the resin material are fused to each other. In addition, the distal side shaft 410 formed of the resin material and the inner tubular shaft 510 formed of the resin material are fused to each other.

If the joining process is performed, the forming material of the inner tubular shaft 510 is melted, and enters the inside of the concave portion 441 of the small diameter portion 429. Similarly, the forming material of the inner tubular shaft 510 also enters the inside of the proximal side concave portion 442 of the inclined portion 428. Therefore, if the lengths before and after the joining process are compared with each other, the outer peripheral length (outer diameter) of a portion (portion joined in a state where the distal side shaft 410, the proximal shaft 420, and the inner tubular shaft 510 overlap each other in the axial direction) covered by the heat-shrinkable tube 650 becomes smaller after the joining process is performed. Therefore, the outer peripheral length of the joint region S of the catheter shaft 110 can be formed so as to be decreased.

In addition, in the heat-shrinkable tube coating process, the distal portion 651 of the heat-shrinkable tube 650 is disposed on the proximal side from the distal opening 421a of the proximal shaft 420. Accordingly, when the joining process is performed, the resin material can be prevented from flowing into the distal opening 421a. In particular, the proximal shaft 420 according to the present embodiment has no opening which communicates with the outside of the lumen 425 except for the distal opening 421a and the proximal opening 423a. Accordingly, when the joining process is performed, it is possible to reliably prevent the resin material from flowing into the proximal shaft 420.

In addition, in the heat-shrinkable tube coating process, the distal portion 651 of the heat-shrinkable tube 650 is disposed on the distal side from the boundary portion 430 between the small diameter portion 429 and the inclined portion 428. The proximal portion 653 of the heat-shrinkable tube 650 is disposed on the proximal side from the proximal portion 653 of the distal side shaft 410. Accordingly, the inner tubular shaft 510 can be suitably fused to the small diameter portion 429 and the inclined portion 428. The distal side shaft 410 and the proximal shaft 420 can be suitably fused to each other on the proximal side of the distal side shaft 410.

Next, a mandrel removing process is performed.

As illustrated in FIG. 9, after the joining process is performed, a mandrel 610 is removed from the lumen 215 of the inner tubular shaft 510.

Next, a guide wire proximal opening forming process is performed.

Figure 10A:
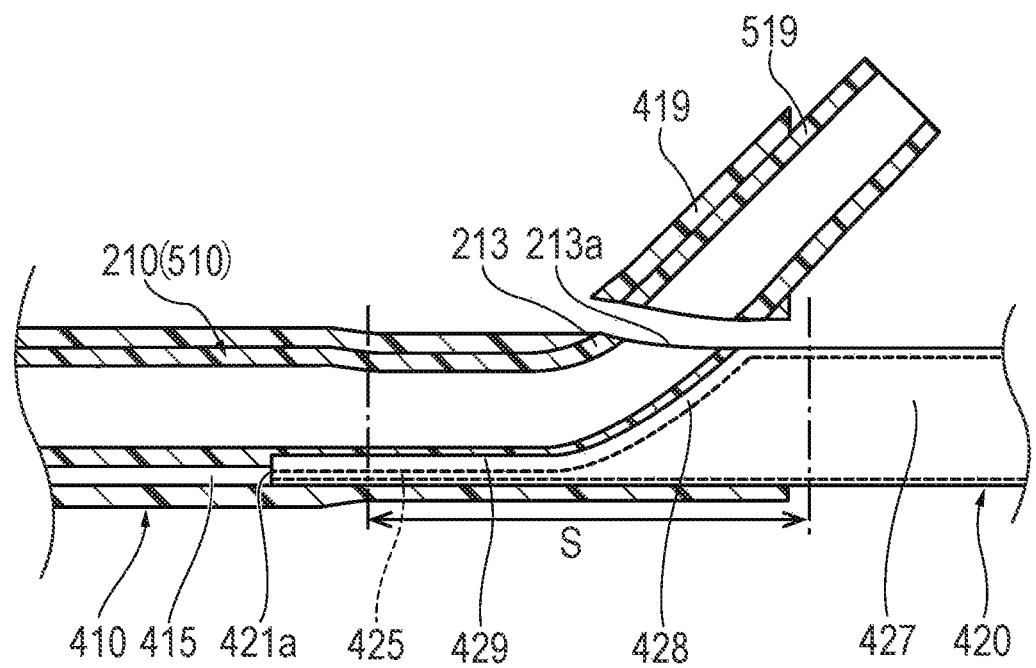
FIG. 10A is a view for describing a manufacturing method of the elongated member for the balloon catheter according to the embodiment, and is a view illustrating a state of a proximal opening forming process.

As illustrated in FIG. 10A, a portion 519 of the inner tubular shaft 510 which protrudes from the outer surface of the proximal shaft 420 is cut out so as to form the guide wire proximal opening 213a which is open on the outer surface of the distal side shaft 410.

Figure 10B:
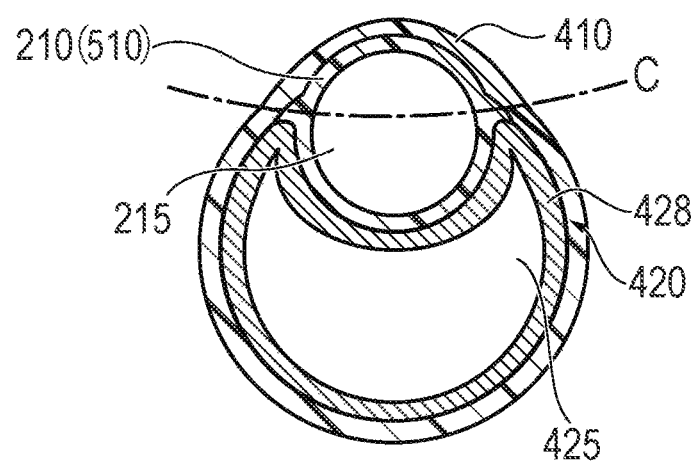
FIG. 10B is a view illustrating an axially orthogonal cross section of each shaft when the proximal opening forming process is performed.

FIG. 10B illustrates the axially orthogonal cross-sectional view of a portion for forming the guide wire proximal opening 213a. For example, the guide wire proximal opening 213a can be formed by cutting the protruding portion 519 of the inner tubular shaft 510 along a cutting position C illustrated by a single-dot chain line in FIG. 10B. Note that, a portion 419 of the distal side shaft 410 which protrudes from the outer surface of the proximal shaft 420 may be cut out together with the protruding portion 519 of the inner tubular shaft 510.

In the axially orthogonal cross section, the cutting position C can be appropriately changed within a range where the proximal shaft 420 formed of the metal material is not included in a cutting object. In addition, for example, the cutting can be performed using a known tool equipped with a cutting blade capable of cutting the inner tubular shaft 510.

The balloon catheter 1 can be manufactured by attaching the balloon 10 and the hub 20 to the catheter shaft 110 manufactured in the above-described manufacturing processes.

Hereinafter, an operation effect of the manufacturing method of the balloon catheter 1 and the catheter shaft 110 according to the present embodiment will be described.

The balloon catheter 1 according to the present embodiment includes the distal side shaft 410 formed of the resin material, the proximal shaft 420 formed of the metal material which is disposed on the proximal side of the distal side shaft 410, the inner tubular shaft 510 which is disposed in the lumen 415 of the distal side shaft 410 and which forms the guide wire lumen 215 into which the guide wire w is insertable, and the balloon 10 which is fixed to the distal side of the inner tubular shaft 510 and the distal side of the distal side shaft 410. The proximal shaft 420 has the main body portion 427, the inclined portion 428 which is disposed on the distal side of the main body portion 427 and in which a portion of the outer peripheral surface of the proximal shaft 420 is inclined, and the small diameter portion 429 which is disposed on the distal side of the inclined portion 428 and which has the distal opening 421a formed in the small diameter portion 429. The small diameter portion 429 has the concave portion 441 recessed to the lumen 425 side of the proximal shaft 420 in the cross section perpendicular to the axial direction of the proximal shaft 420. The inner tubular shaft 510 is disposed along the inclined portion 428 and the concave portion 441, and is open on the outer surface of the distal side shaft 410, thereby forming the guide wire proximal opening 213a. The distal side shaft 410 is joined to the proximal shaft 420 at the small diameter portion 429 on the proximal side from the distal opening 421a of the proximal shaft 420. Then, the distal opening 421a of the proximal shaft 420 is disposed on the distal side from the guide wire proximal opening 213*a*.

According to the balloon catheter 1 of the present embodiment configured as described above, the inner tubular shaft 510 is disposed along the inclined portion 428 of the proximal shaft 420 formed of the metal material and the concave portion 441 of the small diameter portion 429. Accordingly, the lumen 215 (guide wire lumen) of the inner tubular shaft 510 can be prevented from communicating with the lumen 425 (inflation lumen 315) of the proximal shaft 420 in the vicinity of the guide wire proximal opening 213*a* of the inner tubular shaft 510. Therefore, when the inflation fluid is injected into the balloon 10, it is possible to more reliably prevent leakage between the lumen 215 of the inner tubular shaft 510 and the lumen 425 of the proximal shaft 420.

In addition, according to the balloon catheter 1 of the present embodiment, in the portion where the three shafts such as the distal side shaft 410, the inner tubular shaft 510, and the proximal shaft 420 which configure the catheter shaft 110 are joined to each other, the inner tubular shaft 510 is disposed in the concave portion 441 of the proximal shaft 420. Therefore, the outer peripheral length (outer diameter) of the joined portion can be decreased. Therefore, it is possible to provide the catheter shaft 110 having the decreased outer peripheral length.

In addition, according to the balloon catheter 1 of the present embodiment, the proximal shaft 420 formed of the metal material is joined to the distal side shaft 410 and the inner tubular shaft 510, and integrally extends to the distal side from the guide wire proximal opening 213*a*. Accordingly, pushing ability of the catheter shaft 110 is improved.

According to the balloon catheter 1 of the present embodiment, in the cross section perpendicular to the axial direction of the proximal shaft 420, the concave portion 441 has the first curved portion 441*a* curved (for example, mostly or to the greatest extent) to the lumen 425 side of the proximal shaft 420, and the second curved portion 441*b* and the third curved portion 441*c* which are curved outward of the guide wire lumen 215 while being apart from the first curved portion 441*a*. Then, the second curved portion 441*b* and the third curved portion 441*c* are substantially symmetrical with each other in the cross section perpendicular to the axial direction of the proximal shaft 420.

The concave portion 441 is formed in the cross-sectional shape having the respective curved portions 441*a*, 441*b* and 441*c* as described above. Accordingly, while the cross-sectional area of the lumen 425 (inflation lumen 315) of the proximal shaft 420 is increased, the inner tubular shaft 510 can be more reliably disposed along the small diameter portion 429 and the inclined portion 428. In this way, the cross-sectional area of the distal opening 421*a* of the proximal shaft 420 can be increased. Therefore, the inflation fluid can be easily injected and discharged. In addition, the inner tubular shaft 510 is located along the small diameter portion 429 and the inclined portion 428. Accordingly, the outer peripheral length of the catheter shaft 110 can be decreased.

According to the balloon catheter 1 of the present embodiment, at least a portion of the guide wire lumen 215 is surrounded by the concave portion 441 in the cross section perpendicular to the axial direction of the proximal shaft 420. Therefore, the outer peripheral length of the portion where the distal side shaft 410, the inner tubular shaft 510, and the proximal shaft 420 are joined to each other can be further decreased. In addition, the inner tubular shaft 510 can be more reliably disposed along the small diameter portion 429 and the inclined portion 428.

According to the balloon catheter 1 of the present embodiment, the inclined portion 428 has the proximal side concave portion 442 recessed to the lumen 425 side of the proximal shaft 420 in the cross section perpendicular to the axial direction of the proximal shaft 420. Therefore, the outer peripheral length of the catheter shaft 110 in the inclined portion 428 can be decreased, and the inner tubular shaft 510 can be more reliably disposed along the small diameter portion 429 and the inclined portion 428.

A method of manufacturing the catheter shaft 110 according to the present embodiment has an assembly process including the preparation process of preparing the distal side shaft 410 formed of the resin material, the inner tubular shaft 510 formed of the resin material, and the proximal shaft 420 formed of the metal material, the proximal shaft 420 possessing the main body portion 427, the inclined portion 428 which is disposed on the distal side of the main body portion 427 and in which a portion of the outer peripheral surface is inclined, and the small diameter portion 429 disposed on the distal side of the inclined portion 428 and having the distal opening 421*a* the inner tubular shaft disposition process of disposing the inner tubular shaft 510 in the lumen 415 of the distal side shaft 410, the mandrel disposition process of inserting the mandrel 610 into the lumen 215 of the inner tubular shaft 510, and the proximal shaft disposition process of disposing the proximal shaft 420 in the lumen 415 of the distal side shaft 410 while the inner tubular shaft 510 is located along the inclined portion 428 and the small diameter portion 429 of the proximal shaft 420, the heat-shrinkable tube coating process of disposing the heat-shrinkable tube 650 so as to cover a portion of the distal side shaft 410, and the joining process of joining the distal side shaft 410, the proximal shaft 420, and the inner tubular shaft 510 to each other by heating and shrinking the heat-shrinkable tube 650.

As described above, according to the manufacturing method of the present embodiment, the proximal shaft disposition process is performed as follows. While the inner tubular shaft 510 is located along the inclined portion 428 and the small diameter portion 429 of the proximal shaft 420 formed of the metal material, the proximal shaft 420 is disposed in the lumen 415 of the distal side shaft 410. In this manner, the lumen 415 of the distal side shaft 410 and the lumen 425 of the proximal shaft 420 are brought into a communication state. In this state, the joining process of joining the distal side shaft 410, the inner tubular shaft 510, and the proximal shaft 420 is performed. The proximal shaft 420 is formed of the metal material. Accordingly, it is possible to prevent the cross-sectional shape of the proximal shaft 420 from being excessively deformed due to influence of heat and pressure which are applied when the joining process is performed. Accordingly, when the joining process is performed, it is not necessary to dispose the mandrel in order to form the inflation lumen 315 between the lumen 425 of the proximal shaft 420 and the outer peripheral surface of the inner tubular shaft 510. Therefore, the catheter shaft 110 can be rather easily manufactured.

According to the method of manufacturing the catheter shaft 110 of the present embodiment, the heat-shrinkable tube coating process includes the heat-shrinkable tube disposition process of disposing the distal portion 651 of the heat-shrinkable tube 650 on the distal side from the boundary portion 430 between the small diameter portion 429 and the inclined portion 428, which is the proximal side from the distal opening 421*a* of the proximal shaft 420, and disposing the proximal portion 653 of the heat-shrinkable tube 650 on the proximal side from the proximal portion 413 of the distal side shaft 410.

The heat-shrinkable tube disposition process is performed as described above. In this manner, the resin material can be prevented from flowing into the distal opening 421a when the joining process is performed. In addition, the inner tubular shaft 510 can be fused to the small diameter portion 429 and the inclined portion 428, and the distal side shaft 410 and the proximal shaft 420 can be fused to each other on the proximal side of the distal side shaft 410. In this manner, while leakage from the tube wall is prevented in the vicinity of the guide wire proximal opening 213a, it is possible to form the joint region S where the distal side shaft 410, the proximal shaft 420, and the inner tubular shaft 510 are suitably joined to each other.

A method of manufacturing the catheter shaft 110 according to the present embodiment has the mandrel removing process of removing the mandrel 610 from the lumen 215 of the inner tubular shaft 510 after the joining process is performed, and the guide wire proximal opening forming process of cutting out the portion 519 of the inner tubular shaft 510 which protrudes from the outer surface of the proximal shaft 420 and forming the guide wire proximal opening 213a which is open on the outer surface of the distal side shaft 410. Therefore, the guide wire proximal opening 213a can be formed in the catheter shaft 110 after the joining.

According to the method of manufacturing the catheter shaft 110 of the present embodiment, the small diameter portion 429 has the concave portion 441 recessed to the lumen side of the proximal shaft 420 in the cross section perpendicular to the axial direction of the main body portion 427. In the proximal shaft disposition process, while the inner tubular shaft 510 is located along the concave portion 441 of the small diameter portion 429, the proximal shaft 420 is disposed in the lumen 415 of the distal side shaft 410. In this way, the inner tubular shaft 510 is disposed along the concave portion 441 and the inclined portion 428 of the small diameter portion 429. In this manner, the outer peripheral length of the catheter shaft 110 after the joining can be reduced.

Hitherto, the balloon catheter and the manufacturing method of the elongated member for the balloon catheter according to the present invention have been described with reference to the embodiment. However, the present invention is not limited to only the content described above in the embodiment, and can be appropriately modified, based on the description of appended claims.

For example, the cross-sectional shape of the concave portion or the proximal side concave portion is not particularly limited as long as the inner tube can be disposed on the outer surface of the proximal shaft. Any shape other than the shape described with reference to the drawings may be employed. In addition, the proximal side concave portion may not be disposed in the inclined portion.

In addition, the balloon catheter is not limited to a use for widening the lesion area (stenosed site), and may be configured to serve as a balloon catheter for stent delivery, for example.

In addition, a structure of each portion or disposition of a member of the balloon catheter described in the embodiment can be appropriately modified. It is possible to appropriately omit the use of additional members described with reference to the drawings, and to use other additional members. Similarly, it is also possible to appropriately modify each process relating to the manufacturing method of the elongated member for the balloon catheter and equipment used for the manufacturing.

The detailed description above describes a balloon catheter, and a manufacturing method of an elongated member for a balloon catheter. The invention is not limited, however, to the precise embodiments and variations described. Various changes, modifications and equivalents can be effected by one skilled in the art without departing from the spirit and scope of the invention as defined in the accompanying claims. It is expressly intended that all such changes, modifications and equivalents which fall within the scope of the claims are embraced by the claims.

What is claimed is:
1. A balloon catheter comprising:
a distal side shaft formed of a resin material;
a proximal shaft disposed on a proximal side of the distal side shaft and formed of a metal material, the proximal shaft having a main body portion, an inclined portion disposed on a distal side of the main body portion and in which an outer peripheral surface of the proximal shaft is partially inclined, and a small diameter portion disposed on a distal side of the inclined portion and having a distal opening, and wherein in a cross section perpendicular to an axial direction of the proximal shaft, the small diameter portion having a concave portion recessed to a lumen side of the proximal shaft;
an inner tubular shaft disposed in a lumen of the distal side shaft and forming a guide wire lumen into which a guide wire is insertable, the inner tubular shaft being disposed along the inclined portion and the concave portion, the inner tubular shaft being open on an outer surface of the distal side shaft forming a guide wire proximal opening, and wherein the distal side shaft is joined to the proximal shaft at the small diameter portion on the proximal side from the distal opening of the proximal shaft, and the distal opening of the proximal shaft is disposed on the distal side from the guide wire proximal opening; and
a balloon fixed to a distal side of the inner tubular shaft and a distal side of the distal side shaft.

2. The balloon catheter according to claim 1, wherein in the cross section perpendicular to the axial direction of the proximal shaft, the concave portion has a first curved portion curved to the lumen side of the proximal shaft, and a second curved portion and a third curved portion which are curved outward of the guide wire lumen while being apart from the first curved portion; and
the second curved portion and the third curved portion being substantially symmetrical with each other, in the cross section perpendicular to the axial direction of the proximal shaft.

3. The balloon catheter according to claim 1, wherein at least a portion of the guide wire lumen is surrounded by the concave portion in the cross section perpendicular to the axial direction of the proximal shaft.

4. The balloon catheter according to claim 1, wherein the inclined portion has a proximal side concave portion recessed to the lumen side of the proximal shaft in the cross section perpendicular to the axial direction of the proximal shaft.

5. The balloon catheter according to claim 1, wherein the metal material of the proximal shaft is aluminum, stainless steel, brass, or Ni—Ti.

6. The balloon catheter according to claim 1, wherein the resin material of the distal side shaft is polyethylene, polypropylene, polybutene, ethylene-propylene copolymer, and ethylene-vinyl acetate copolymer, or ionomer.

7. The balloon catheter according to claim 1, wherein the resin material is polyvinyl chloride resin, polyamide, polyamide elastomer, polyester, polyester elastomer, polyurethane, or polytetrafluoroethylene.

8. The balloon catheter according to claim 1, wherein the inner tubular shaft is formed of a resin material.

9. The balloon catheter according to claim 1, further comprising:
an inflation lumen on the distal side shaft, the inflation lumen being in fluid communication with the main body portion of the proximal shaft and located between an outer surface of the inner tubular member and the distal side shaft, and wherein the inflation lumen is configured to provide an inflation fluid to the balloon of the balloon catheter.

10. The balloon catheter according to claim 1, further comprising:
an X-ray contrast marker arranged on the inner tubular shaft in a central position in an axial direction of an inflatable portion of the balloon.

11. The balloon catheter according to claim 1, further comprising:
a hub configured to be connected to a proximal end of the proximal portion of the proximal shaft of the balloon catheter, the hub configured to supply an inflation fluid to the balloon catheter.

12. A treatment method comprising:
introducing a balloon catheter into a living body, the balloon catheter including a distal side shaft formed of a resin material, a proximal shaft disposed on a proximal side of the distal side shaft and formed of a metal material, the proximal shaft having a main body portion, an inclined portion disposed on a distal side of the main body portion and in which an outer peripheral surface of the proximal shaft is partially inclined, and a small diameter portion disposed on a distal side of the inclined portion and having a distal opening, and wherein in a cross section perpendicular to an axial direction of the proximal shaft, the small diameter portion having a concave portion recessed to a lumen side of the proximal shaft; and an inner tubular shaft disposed in a lumen of the distal side shaft and forming a guide wire lumen into which a guide wire is insertable, the inner tubular shaft being disposed along the inclined portion and the concave portion, the inner tubular shaft being open on an outer surface of the distal side shaft forming a guide wire proximal opening, and wherein the distal side shaft is joined to the proximal shaft at the small diameter portion on the proximal side from the distal opening of the proximal shaft, and the distal opening of the proximal shaft is disposed on the distal side from the guide wire proximal opening, and a balloon fixed to a distal side of the inner tubular shaft and a distal side of the distal side shaft;
introducing a guide wire into the guide wire proximal opening;
advancing the balloon catheter over the guide wire to a stenosed site in the living body; and
inflating the balloon of the balloon catheter into the stenosed site.

13. The treatment method according to claim 12, wherein in the cross section perpendicular to the axial direction of the proximal shaft, the concave portion has a first curved portion curved to the lumen side of the proximal shaft, and a second curved portion and a third curved portion which are curved outward of the guide wire lumen while being apart from the first curved portion; and
the second curved portion and the third curved portion being substantially symmetrical with each other, in the cross section perpendicular to the axial direction of the proximal shaft.

14. The treatment method according to claim 12, wherein at least a portion of the guide wire lumen is surrounded by the concave portion in the cross section perpendicular to the axial direction of the proximal shaft.

15. The treatment method according to claim 12, wherein the inclined portion has a proximal side concave portion recessed to the lumen side of the proximal shaft in the cross section perpendicular to the axial direction of the proximal shaft.

16. The treatment method according to claim 12, further comprising:
detecting a location of the balloon catheter in the living body with an X-ray contrast marker arranged on the inner tubular shaft in a central position in an axial direction of an inflatable portion of the balloon.

* * * * *